US006920876B2

(12) United States Patent
Miller et al.

(10) Patent No.: US 6,920,876 B2
(45) Date of Patent: Jul. 26, 2005

(54) DEVICE FOR ADMINISTRATION OF NITRIC OXIDE TO HORSES SPONTANEOUSLY BREATHING

(75) Inventors: Christopher Miller, North Vancouver (CA); Bryan Perry, West Seneca, NY (US); Robert E. Lee, Camrose (CA); Stephen H. Fairbanks, ElCentro, CA (US)

(73) Assignee: Pulmonox Technologies Corporation, Tolfield (CA)

( * ) Notice: Subject to any disclaimer, the term of this patent is extended or adjusted under 35 U.S.C. 154(b) by 59 days.

(21) Appl. No.: 10/315,539

(22) Filed: Dec. 10, 2002

(65) Prior Publication Data

US 2003/0150457 A1 Aug. 14, 2003

Related U.S. Application Data

(60) Provisional application No. 60/338,943, filed on Dec. 10, 2001.

(51) Int. Cl.[7] .............................................. A62B 7/00
(52) U.S. Cl. ........................ 128/204.18; 128/204.21; 128/204.23; 128/200.24; 128/203.12; 128/205.22; 128/207.14
(58) Field of Search .................... 128/200.24, 203.12, 128/205.22, 207.14, 205.23, 205.24

(56) References Cited

U.S. PATENT DOCUMENTS

| 5,062,423 A | * | 11/1991 | Matson et al. | 128/207.15 |
|---|---|---|---|---|
| 5,713,349 A | * | 2/1998 | Keaney | 128/204.23 |
| 5,765,548 A | * | 6/1998 | Perry | 128/200.24 |
| 5,839,433 A | * | 11/1998 | Higenbottam | 128/204.21 |
| 5,918,596 A | * | 7/1999 | Heinonen | 128/204.21 |
| 6,109,260 A | * | 8/2000 | Bathe | 128/203.12 |
| 6,125,846 A | * | 10/2000 | Bathe et al. | 128/202.22 |
| 6,142,147 A | * | 11/2000 | Head et al. | 128/204.21 |
| 6,164,276 A | * | 12/2000 | Bathe et al. | 128/202.22 |
| 6,581,592 B1 | * | 6/2003 | Bathe et al. | 128/202.22 |
| 6,612,306 B1 | * | 9/2003 | Mault | 128/204.22 |
| 6,694,969 B1 | * | 2/2004 | Heinonen et al. | 128/200.24 |

* cited by examiner

*Primary Examiner*—Henry Bennett
*Assistant Examiner*—Nihir Patel
(74) *Attorney, Agent, or Firm*—Sidley Austin Brown & Wood LLP

(57) ABSTRACT

The present invention is directed to a nitric gas dispenser for mammals on the run. The dispenser has a housing that contains a valve mechanism. The valve mechanism is interconnected between a nitric gas dispersal component that provides nitric gas at a desired pressure and a gas delivery system that provides the nitric gas at the desired pressure to the mammal. The valve mechanism controls the flow of the nitric gas between the nitric gas dispersal component and the gas delivery system. The dispenser also has a pressure sensor that is positioned along the gas delivery system and determines when the mammal is taking a breadth. If the pressure sensor determines the mammal is taking a breadth, the pressure sensor transmits a breadth signal to a microprocessor. The microprocessor then determines if the mammal is within a prescribed time frame for the mammal to be administered nitric gas. If the microprocessor determine the mammal is within the prescribed time frame, the microprocessor transmits an open signal to the valve mechanism to release a predetermined amount of nitric oxide gas to the mammal.

5 Claims, 5 Drawing Sheets

DEVICE FOR ADMINISTRATION OF NITRIC OXIDE TO HORSES SPONTANEOUSLY BREATHING

CLAIM OF PRIORITY

This application claims priority to U.S. provisional patent application Ser. No. 60/338,943, filed on Dec. 10, 2001.

FIELD OF THE INVENTION

The present invention is directed to a delivery system of nitric oxide to a mammal.

BACKGROUND OF THE INVENTION

Applicant admits there are numerous devices and methods to administer nitric oxide to a mammal. One of those devices contains a mask that surrounds the mammal's breathing orifices. This is a conventional method to deliver nitric oxide to a mammal. That method, however, would be impractical for delivering nitric oxide to a moving mammal, that simultaneously still has to breathe enormous quantities of air. The present invention solves this problem.

SUMMARY OF THE INVENTION

The present invention is directed to a nitric gas dispenser for mammals on the run. The dispenser has a housing that contains a valve mechanism. The valve mechanism is interconnected between a nitric gas dispersal component that provides nitric gas at a desired pressure and a gas delivery system that provides the nitric gas at the desired pressure to the mammal. The valve mechanism controls the flow of the nitric gas between the nitric gas dispersal component and the gas delivery system. The dispenser also has a pressure sensor that is positioned along the gas delivery system and determines when the mammal is taking a breadth. If the pressure sensor determines the mammal is taking a breadth, the pressure sensor transmits a breadth signal to a microprocessor. The microprocessor then determines if the mammal is within a prescribed time frame for the mammal to be administered nitric gas. If the microprocessor determine the mammal is within the prescribed time frame, the microprocessor transmits an open signal to the valve mechanism to release a predetermined amount of nitric oxide gas to the mammal.

BRIEF DESCRIPTION OF THE DRAWINGS

The various figures of the drawing depict illustrative and exemplary forms of the nitric oxide delivery device and method. Throughout the several figures, identical reference characters represent identical structure wherein.

DETAILED DESCRIPTION OF THE PREFERRED EMBODIMENTS

Figure 1:
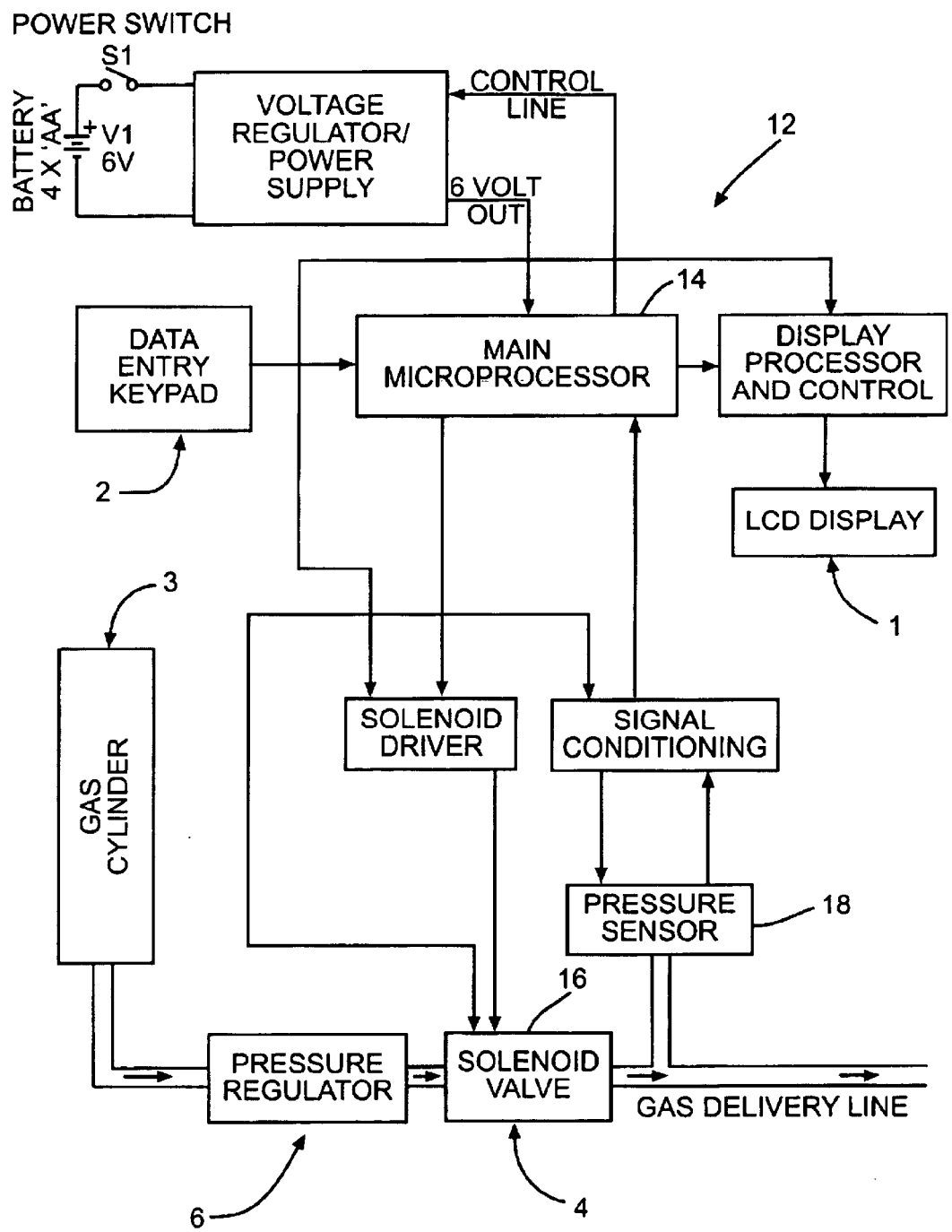
FIG. 1 is a schematic drawing of the electromechanical gas delivery device.
Figure 2:
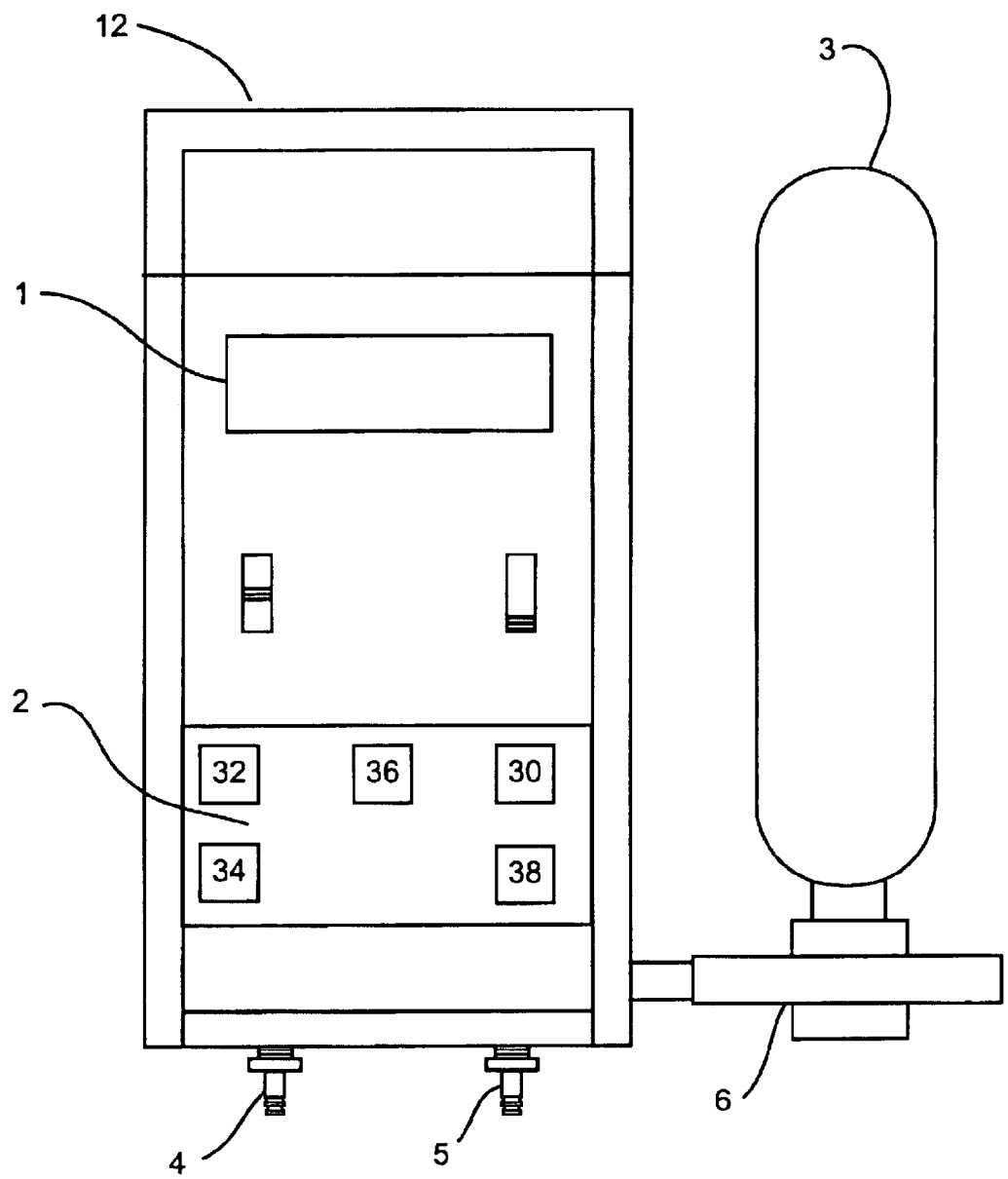
FIG. 2 is a pictorial representation of the device referred to FIG. 1.

FIG. 1 illustrates a block diagram representation of the device 12 that is pictorially illustrated in FIG. 2. With reference to FIG. 1, the device 12 has a power source 100. The power source can be an electrical outlet if the user of the device is going to work out on a treadmill or a battery if the user will be working away from a confined environment like a track. The power source 100 provides sufficient voltage and charge to properly operate the device 12. The device 12 also has a main microprocessor 14 that controls the operation of a solenoid valve 16, also within the device 12. The solenoid valve 16 operates in conjunction with operating parameters that are entered via a data entry keypad 2 and the input from a pressure sensor 18.

The operating parameters and the operating status of the device 12 are displayed on an LCD display 1. Along with the LCD display 1, the device 12 has a nitric oxide gas supply 3, preferably a cylinder. In that cylinder is nitric oxide having a pressure of 1800 to 2200 pounds per square inch (psi).

The device 12 also has a pressure regulator 6. The pressure regulator 6 reduces the pressure of the nitric oxide to less than 100 psi so it can be administered to the mammal, preferably a horse, without damaging the mammal's organs from too much pressure.

Calibrating the flow through the solenoid valve 16 is obtained by selecting the pressure of the pressure regulator 6 and controlling the time that the solenoid valve 16 is open. Thereby, the valve 16 allows a precise amount of nitric oxide to be delivered through a gas delivery line 4, which delivers the nitric oxide to the mammal, preferably a horse. The pressure sensor 18 is designed to detect a drop in pressure in the gas delivery line 4, when the horse initiates a breath. This pressure drop signals the main processor 14 to open the solenoid valve 6 for a pre-programmed period of time. Among the parameters that are programmed into the device are: Total Breaths, Start Delay, Pulse Time, Pulse Delay, and Re-trigger Lock.

The programmable parameters are defined as follows:

Total Breaths: This parameter is the number of breaths programmed into a run. Each time a breath is detected as identified above, a pulse of nitric oxide gas is injected into the breath of mammal. Breaths that occur during a locked out time of the run are not counted as breaths. After the programmed number of breaths are counted, the run stops automatically and nitric oxide gas is no longer injected into any breaths of the mammal. This number can be set anywhere from 0 to 100 breaths. If the number is set at 0 then the auto shutoff is disabled and breaths will be injected with nitric oxide until the user stops the run.

Start Delay: This parameter is the programmed delay time in minutes that the user can set. The injection of nitric oxide gas into each breath will begin automatically after "Start Delay" minutes. It will then continue for the number of Total Breaths and then the device 12 stops automatically.

Pulse Time: This parameter is the length of time that the solenoid valve 16 will open for delivery of nitric oxide gas. The resolution is 0.1 seconds and the range is 0.1 sec to 0.9 seconds. If the regulator is set at 50 psi then each second of the solenoid valve 16 opening 31 cc of nitric oxide gas. If the regulator pressure is set at 30 psi then each 0.1 sec solenoid valve 16 opening represents 21 cc of nitric oxide gas. For example, if the regulator is set at 50 psi and the pulse time is set at 0.3 seconds then each detected breath will be injected with a pulse of 0.3 seconds or about 90 cc of nitric oxide gas.

Pulse delay: This parameter is the length of time that the machine waits after detecting the beginning of a breath before opening the solenoid valve 16 to inject a pulse of nitric oxide gas. This allows the user to control the position of the bolus of nitric oxide gas in the breath. For example, if the user sets the solenoid valve 16 at 0.4 seconds, then 0.4 seconds after the beginning of the breath is detected the solenoid valve 16 will open to inject the nitric oxide pulse.

Retrigger Lock: This parameter is the total time that the machine will ignore new breaths beginning at the detection of a new breath. If this parameter is set at 4.5 seconds then the device 12 will wait, after detecting a breath, for 4.5 seconds before recognizing a new breath. Full or half breaths that are initiated by the animal during this lockout time will not be counted and no nitric oxide will be injected. If the breath is initiated before the lockout expires and the animal is still inhaling when the lockout expires then it will be recognized as a new breath and it will be counted and injected with nitric oxide.

With reference to FIG. 2, the data entry keypad 2 contains five active button switches defined as follows:

START/PULSE KEY 30: This key is used to start a run. The user is required to confirm the start by pressing an UP key 32 or to cancel by pressing a DOWN key 34. When a run is in progress, pressing this key will cause the run to pause. The run is then resumed by pressing the UP key 32 or stopping the run by pressing the DOWN key 34.

UP key 32: This key is used to confirm the start of the run, to resume a paused run and also to increment valve changes.

DOWN key 34: This key is used to cancel a started run, end a paused run and also to decrement valve changes.

NEXT key 36: This key is used to switch screen pages on the LCD display 1.

PURGE key 38: This key is used to open the solenoid valve 16 for two seconds to purge the line. This key is not active during a run. The LCD display 1 displays four screen pages, defined as follows:

Each screen page displays a status line. The status variations include NOT RUNNING, WAITING, RUNNING, PAUSED, PURGING and START Pressed.

The main screen page has a row of asterisks on the top line. This is the only screen available when the KEY switch is in the locked position. This screen displays the total breaths detected and also the total breaths that will cause the run to stop.

The second page shows two valves. The first is the START DELAY valve. When the screen first appears the blinking cursor shows the value, which can be changed by pressing either the UP or DOWN key. Pressing the NEXT key switches, the cursor to the second value on the screen which is TOTAL BREATHS.

The third page allows the user to change the PULSE DELAY and the PULSE TIME.

The fourth page allows the user to change the RETRIGGER LOCK.

With reference to FIG. 2, a capped port 5 is depicted. This is an alternate input port fir nitric oxide and is utilized if the device is not used with the small gas cylinder as depicted in FIG. 2. The cap is typically replaced with a quick-connect style fitting for attachment to a standard regulators on a large gas cylinder.

Figure 3:
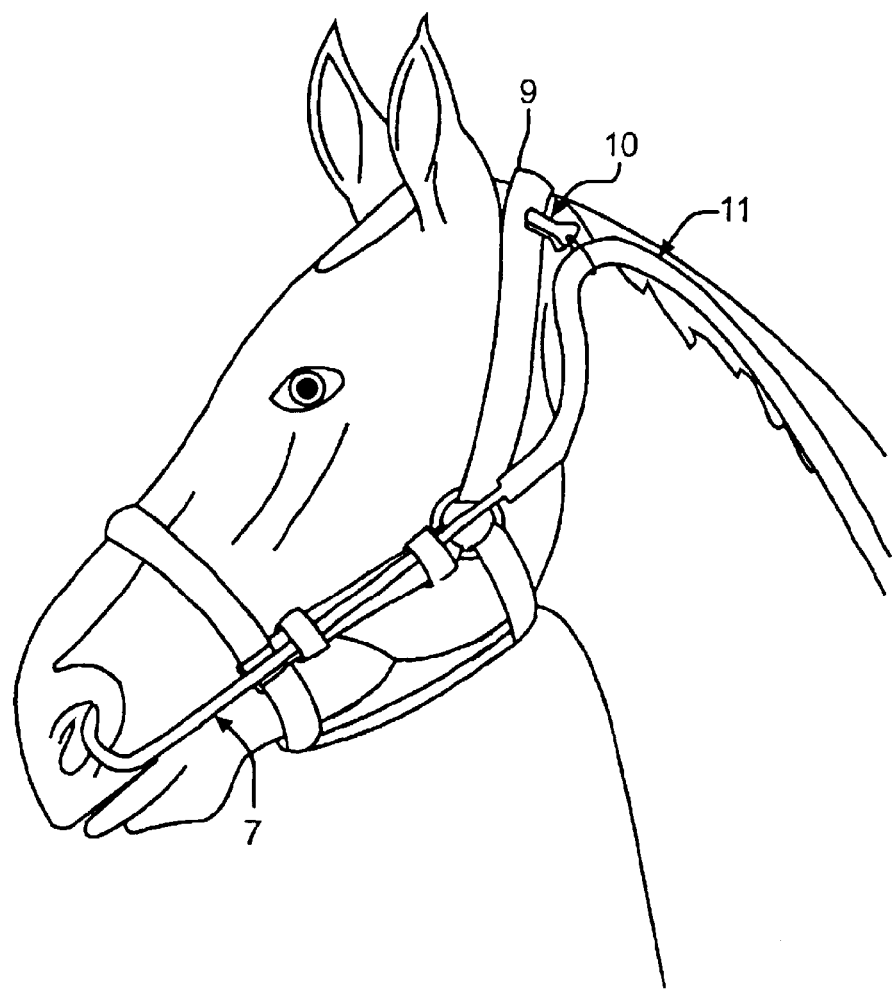
FIG. 3 is a pictorial representation of the method of delivery of the gas to said horse.

FIG. 3 illustrates the method of delivering nitric oxide to the horse. A J-tube 7 made of semi rigid plastic such as styrene is attached to the horses' halter 9 by two hook and loop fabric fasteners. A small clip 10 also secures the delivery line 11 to the halter 9. The delivery tube 11 is typically a clear plastic flexible tubing. The delivery line connects to port 4 shown in FIG. 2.

Figure 4:
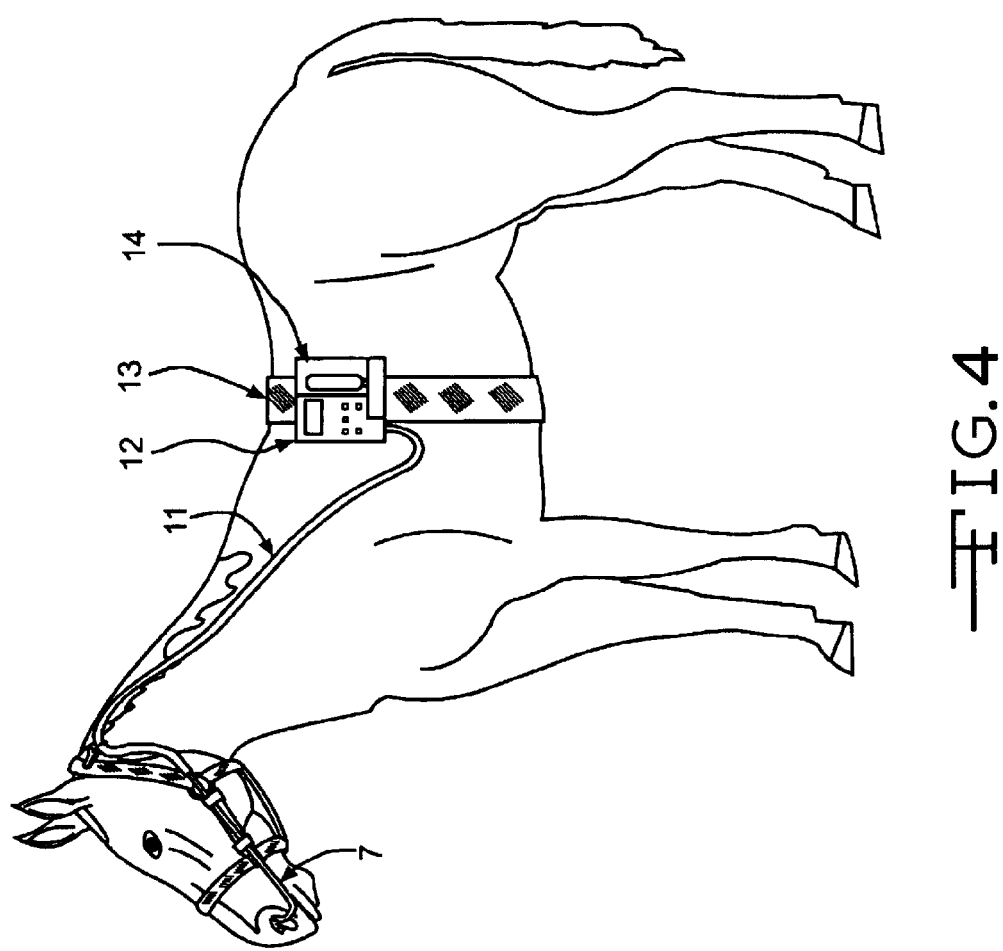
FIG. 4 is a pictorial representation of the overall delivery system.
Figure 5:
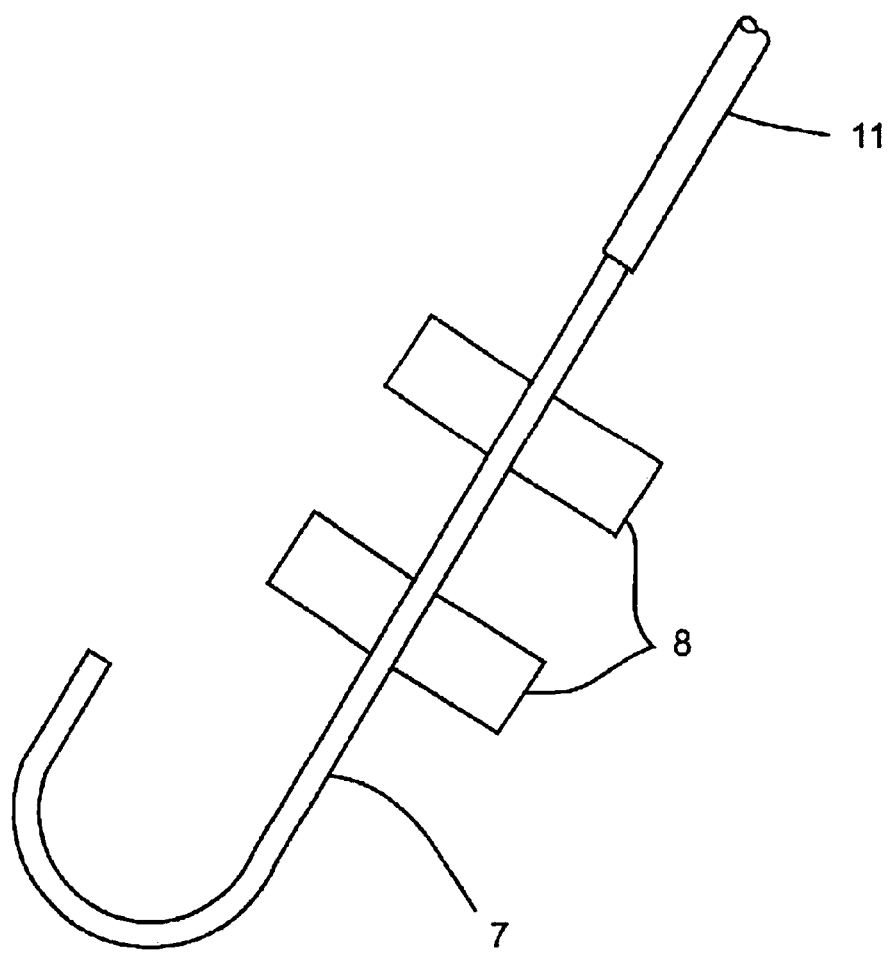
FIG. 5 is a pictorial representation of the J-tube used in conjunction with the device to induce gas into the nostril of said horse.

FIG. 4 shows a typical application in its complete form. The delivery device 12 is shown in a cradle 14 which attaches to a surcingle 13. This provides a convenient method of attaching the device to a horse.

While the preferred embodiment of the invention has been illustrated and described, it will be clear that the invention is not so limited. Numerous modifications, changes, variations, substitutions and equivalents will occur to those skilled in the art without departing from the spirit and scope of the present invention as defined by the appended claims.

We claim:

1. A nitric oxide gas dispenser for mammals, comprising:
    a housing containing a valve mechanism that is interconnected between a nitric oxide gas dispersal component that provides nitric oxide gas at a desired pressure and a gas delivery system transmits the nitric gas directly into, without premixing with other gases, and at the desired pressure to the mammal;
    the valve mechanism controls the flow of the nitric oxide gas between the nitric oxide gas dispersal component and the gas delivery system;
    a pressure sensor is positioned along the gas delivery system and determines when the mammal is taking a breath;
    if the pressure sensor determines the mammal is taking a breath, the pressure sensor transmits a breath signal to a microprocessor, the microprocessor then determines if the mammal is within a prescribed time frame for the mammal to be administered nitric oxide gas;
    if the microprocessor determine the mammal is within the proscribed time frame, the microprocessor transmits an open signal to the valve mechanism to release a predetermined amount of nitric oxide gas directly, without pre-mixing with other gases, into the mammal.

2. The dispenser of claim 1 wherein the nitric oxide gas is transmitted into the nostril of the mammal.

3. The dispenser of claim 1 wherein the prescribed time frame is determined by an operator entering parameters to the microprocessor.

4. The dispenser of claim 3 wherein the housing has a key pad that allows the operator to enter parameter to the microprocessor.

5. The dispenser of claim 3 wherein the parameters are start delay, pulse time, pulse delay, and retrigger lock.

* * * * *